(12) United States Patent
Syfonios

(10) Patent No.: US 9,289,543 B2
(45) Date of Patent: Mar. 22, 2016

(54) HOUSING WITH CLOSURE FLAP

(75) Inventor: Andreas Syfonios, Bergrheinfeld (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 747 days.

(21) Appl. No.: 13/498,721

(22) PCT Filed: Sep. 29, 2010

(86) PCT No.: PCT/EP2010/064448
§ 371 (c)(1),
(2), (4) Date: Mar. 28, 2012

(87) PCT Pub. No.: WO2011/039248
PCT Pub. Date: Apr. 7, 2011

(65) Prior Publication Data
US 2012/0181296 A1   Jul. 19, 2012

(30) Foreign Application Priority Data
Sep. 29, 2009   (DE) .......... 10 2009 045 095

(51) Int. Cl.
*B01D 61/30* (2006.01)
*B01D 65/00* (2006.01)
*E05D 11/00* (2006.01)
*B65D 43/24* (2006.01)
*A61M 1/14* (2006.01)
(Continued)

(52) U.S. Cl.
CPC .............. *A61M 1/14* (2013.01); *A61M 1/1621* (2013.01); *A61M 1/3621* (2013.01); *B01D 61/30* (2013.01); *B01D 65/00* (2013.01); *B65D 43/24* (2013.01); *E05D 11/10* (2013.01); *E05D 11/1028* (2013.01); *A61M 2209/082* (2013.01)

(58) Field of Classification Search
CPC .. B01D 61/28; B01D 61/30; B01D 2209/082; B01D 65/00; A61M 1/16; A61M 1/1621; A61M 1/3621; A61M 1/34; A61M 1/36; B65D 43/16; B65D 43/163; B65D 43/164; B65D 43/165; B65D 43/167; B65D 43/24; B65D 85/38; E05D 11/00; E05D 11/10; E05D 11/1028
USPC ........... 210/321.6, 645, 646, 85–87, 90, 96.1, 210/97, 258, 541; 604/4.01, 5.01, 6.01, 604/6.09, 65, 67; 16/342, 346
See application file for complete search history.

(56) References Cited

U.S. PATENT DOCUMENTS 5,482,440 A   1/1996   Dennehey et al.
7,527,343 B2   5/2009   Oh et al.
(Continued)

FOREIGN PATENT DOCUMENTS

CN   101113656   1/2008
DE   299 09 761   10/2000
(Continued)

*Primary Examiner* — Joseph Drodge
(74) *Attorney, Agent, or Firm* — Jacobson Holman, PLLC.

(57) ABSTRACT

An equipment housing, in particular the housing of a blood treatment device, having a housing wall and a closing flap for closing an opening in the housing wall. The closing flap is rotatably mounted with respect to a coupling element via a second pivot whereby the coupling element is rotatably mounted with respect to the housing wall via a first pivot. With the two pivots, the closing flap 20 can be disposed in at least a second and a third opened working position, in both of which positions the opening in the housing wall is not closed.

20 Claims, 3 Drawing Sheets

(51) Int. Cl.
*E05D 11/10* (2006.01)
*A61M 1/16* (2006.01)
*A61M 1/36* (2006.01)

(56) References Cited

U.S. PATENT DOCUMENTS

| | | | |
|---|---|---|---|
| 7,935,250 B2 * | 5/2011 | Castellano et al. | 210/143 |
| 8,110,104 B2 * | 2/2012 | Crnkovich et al. | 210/321.6 |
| 8,512,553 B2 * | 8/2013 | Cicchello et al. | 210/98 |
| 2002/0147423 A1 | 10/2002 | Burbank et al. | |
| 2005/0005398 A1 * | 1/2005 | Hirtsiefer | 16/346 |
| 2005/0045548 A1 | 3/2005 | Brugger et al. | |
| 2005/0230292 A1 * | 10/2005 | Beden | A61M 1/1037 210/85 |
| 2006/0122551 A1 * | 6/2006 | Brieske | 604/4.01 |
| 2007/0112297 A1 * | 5/2007 | Plahey | A61M 1/28 604/28 |
| 2008/0018131 A1 | 1/2008 | Heath et al. | |
| 2009/0064463 A1 | 3/2009 | Gomoll et al. | |
| 2009/0099498 A1 * | 4/2009 | Demers et al. | 604/6.09 |
| 2009/0107335 A1 | 4/2009 | Wilt et al. | |
| 2009/0107902 A1 * | 4/2009 | Childers | A61M 1/16 210/196 |
| 2010/0116740 A1 * | 5/2010 | Fulkerson et al. | 210/646 |
| 2010/0140149 A1 * | 6/2010 | Fulkerson et al. | 210/85 |
| 2010/0292657 A1 * | 11/2010 | Fontanazzi | A61M 1/3621 604/256 |
| 2011/0187246 A1 | 8/2011 | Shin et al. | |
| 2013/0284648 A1 * | 10/2013 | Grant et al. | 210/137 |

FOREIGN PATENT DOCUMENTS

| | | |
|---|---|---|
| DE | 10 2005 021 540 | 11/2006 |
| DE | 11 2007 000 423 | 11/2008 |
| EP | 1 535 556 | 6/2005 |
| EP | 2 319 551 | 5/2011 |
| JP | 2001269400 | 10/2001 |
| JP | 2003-518964 | 6/2003 |
| WO | WO 2005/038628 | 4/2005 |
| WO | WO 2008/010004 | 1/2008 |
| WO | WO 2009/051669 | 4/2009 |

* cited by examiner

HOUSING WITH CLOSURE FLAP

This is a national stage of PCT/EP10/064,448 filed Sep. 29, 2010 and published in German, which claims the priority of German number 10 2009 045 095.5 filed Sep. 29, 2009, hereby incorporated by reference.

BACKGROUND OF THE INVENTION

1. Field of the Invention

The invention relates to an equipment housing for medical devices comprising a closing flap for servicing purposes.

2. Description of the Related Art

Such equipment housings are frequently used in blood treatment devices such as for example hemodialysis machines. Hemodialysis also encompasses hemofiltration and hemodiafiltration.

With these devices it is necessary to have easy access to the interior of the device for servicing. For this purpose a closing flap, which is attached to one side or to the front of the device via a hinge or pivot, is folded out from the housing. Technical devices such as for example the extracorporeal blood treatment module (EBM) are typically attached to this closing flap. By this means the service engineer can gain easy access to the interior of the device and to all sides of the EBM, since the latter is, at least substantially, outside the interior of the device following the opening of the flap.

In the manufacture of household appliances, hinges are also known which combine a pivoting and a sliding motion, as shown for example in DE 10 2005 021 540 A1 or EP 1,535,556 B1. And according to WO 2008/010004 A1 complex movements of flaps or covers may be realized via multi-section linkages.

In known designs of the closing flap of blood treatment devices, only one pivot axis is usually provided. In these cases the front of the closing flap, on which various adjustment and display units are located, faces downwards when the flap is folded out, so that it is not easily viewable by the service engineer.

SUMMARY OF THE INVENTION

The object of the invention is to overcome the known shortcomings and to provide a cost-effective and robust housing with which the engineer can perform the required servicing tasks in the interior of the device and on the components located on the closing flap, and at the same time easily reach the operating components located on the front side of the closing flap.

This object is achieved by an equipment housing for blood treatment device having a housing wall and a closing flap closing an opening in the housing wall in a first position. A coupling element is rotatably mounted with respect to the housing wall via a first pivot and the closing flap is rotatably mounted with respect to the coupling element via a second pivot. The closing flap can be disposed in at least one defined second working position in which the opening in the housing wall is not closed.

The equipment housing of a blood treatment device according to the invention comprises a housing wall and a closing flap for closing an opening in the housing wall in a first position. A coupling element is thereby rotatably mounted with respect to the housing wall via a first pivot and the closing flap is rotatably mounted with respect to the coupling element via a second pivot. The closing flap is thereby disposable in at least one defined second working position in which the opening in the housing wall is not closed. It is advantageous if the closing flap is also disposable in a third defined working position in which the opening in the housing wall is not closed. The opening is for example a service opening, through which a service engineer can reach components located in the interior of the device or on the rear side of the closing flap. The first and second pivots are preferably arranged parallel and coplanar or parallel to the housing opening and/or the closing flap. Additionally, the first pivot is in particular not collinear with the second pivot; they are thus laterally offset. The working positions are understood as in each case a definite position of the closing flap, which are set using either retention means such as catches, magnets, levers, latches, retaining straps or similar, or using the action of gravity, and in which the closing flap is held in this position due to the specified means. While in a known flap only one pivot is provided, via the additional second pivot the angular position of the closing flap, in the position in which the coupling element is fully folded out, can be altered and disposed such that the service engineer has good access not only to the areas to be serviced but also to the front with its operating and control elements. Because these working positions are stable, the service engineer can work easily in these positions on the closing flap, make adjustments, and reach the interior of the device.

The opening is advantageously located on a housing wall which is substantially vertically aligned. The closing flap can thus be folded out in a downward direction, and brought into one of the respective working positions due to the action of gravity. Because the closing flap covers the opening in the closed position, the operating and control elements arranged on the closing flap are also vertically aligned for the user in this position, and thus easily readable.

The closing flap can further be mounted with respect to the equipment housing via no additional pivots and/or coupling elements. This formulation encompasses the fact that no additional intervening pivots are provided on either the closing flap or the coupling element. The coupling element according to the invention can, however, have a plurality of parts, for instance using a plurality of parts of identical or similar design arranged in parallel with bearing points which lie on the same pivot axes. While the guiding of components via multi-section coupling elements, such as for example four-bar linkages, is known in mechanics, the proposed design provides a simple and cost-effective solution.

Furthermore, the closing flap is also guided in its movement with respect to the equipment housing without the use of linear guides. A linear guide generally brings with it the danger of a twisting of the guide, it involves higher production costs, and it is more susceptible to wear. The present invention thus offers an advantage in the form of exact and cost-effective guiding. This formulation encompasses the provision of mountings which are not in the form of linear guides for preferably both the closing flap and the coupling element.

In a further embodiment a locking mechanism is provided between the coupling element and the closing flap. It is preferable that when the locking mechanism is engaged the closing flap in the second working position is substantially vertically aligned. The term "vertical" encompasses in particular angular deviations of +/−15°, preferably +/−5°, from the vertical. Due to the vertical alignment the service engineer can easily read the operating and control elements, and the closing flap is secured against pivoting out of this position.

The locking mechanism can be realized in particular by latches or hooks which can be manually opened or closed, or by spring catches, or by magnetic or friction means, or by the utilization of gravity. The locking mechanism can also have a plurality of locking points.

If the wall of the housing is designed slightly inclined, sloping as it ascends or correspondingly curved, it is advantageous to design the inclination of the closing flap to be parallel to the side wall.

It is advantageous if the closing flap tends to pivot due to the action of gravity from the second working position to the third working position. In this case the third stable working position is a position in which the opening in the housing wall is open and the closing flap is not vertical. A locking mechanism as described above can be alternatively provided at the third working position.

Advantageously the mounting of the closing flap against the coupling element can have a longitudinal slot, via which the closing flap can be released from the coupling element (30) and in particular removed. Such a longitudinal slot can be formed as a U-shaped receptacle in the coupling element, such that an axle or bolt in the closing flap presses into the bottom of the "U" due to the action of gravity. For servicing and replacement purposes, the closing flap can thereby be easily removed by being lifted. Naturally, it is possible to reverse the functions by exchanging the receptacle and the bolt with each other. If necessary this removal can be possible only following the release of a retaining element such as a latch or similar. A stop can also be provided, which prevents simple sliding out from the U-shaped receptacle and allows removal only by means of a series of movements in different directions.

To improve stability, and in particular torsional stiffness, two or more substantially mirror-symmetrical or identical coupling elements can also be provided, aligned parallel to each other. The axes of the bearings are thereby collinear.

In a further embodiment, the coupling element can be bow-shaped; a lower limb of the bow remains within the equipment housing in all three positions and an upper limb of the bow is guided through the opening out of the housing in the opened working positions. The term "bow" is here to be understood in a broad sense, and is to encompass in particular any mechanical design of the coupling element in which the bearings of the pivots are so related to each other that a clear space is formed at least partially between them, in which the housing wall can be partially accommodated during the transition to one of the opened working positions. Through this embodiment, the coupling element can be guided completely into the interior of the housing under the said opening, thereby bringing an advantage from the point of view of optical design.

Operating controls for the device are advantageously disposed on the outer side of the closing flap. These include electrical or mechanical adjustment devices, operating elements, displays, or (hose) pumps, peristaltic pumps, fasteners, valves or similar.

Additionally, the access area to the opening in the housing wall can be greater in the third working position than in the second working position. The said access area is defined as the space in front of the opening at a distance of between 0 and 60 cm outwards from the housing wall. By folding the closing flap away from the second into the third working position about the second pivot, this space is increased and the interior of the housing is thereby more easily accessible for assembly work. If only one (lower) pivot were provided, the access area could be increased only by increasing the tilt angle of this pivot. This would however have the disadvantage that the distance from the closing flap to the housing would also increase, creating the problem that correspondingly longer connecting cables and hoses would have to be employed. Through the defined third working position, firstly there is better clearance in front of the opening, and additionally there is no necessity to increase suitably the distance mentioned above, and thus the length of the supply lines.

Additionally in the third working position, the opening angle of the closing flap can be greater than the opening angle of the coupling element. The "opening angle" is understood as the angular difference of the rotation of the applicable element from the first position into the third working position. This angle is not the relative movement in the pivot, but is relative to a locally fixed reference point, such as for example the side wall. Due to this angular position, the rear side of the parts mounted on the inside of the closing flap is more easily accessible from above for servicing purposes in the folded out third working position.

BRIEF DESCRIPTION OF THE DRAWINGS

The invention is elucidated with the aid of the drawings. The drawings show.

DETAILED DESCRIPTION OF THE PREFERRED EMBODIMENTS

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

Figure 1:
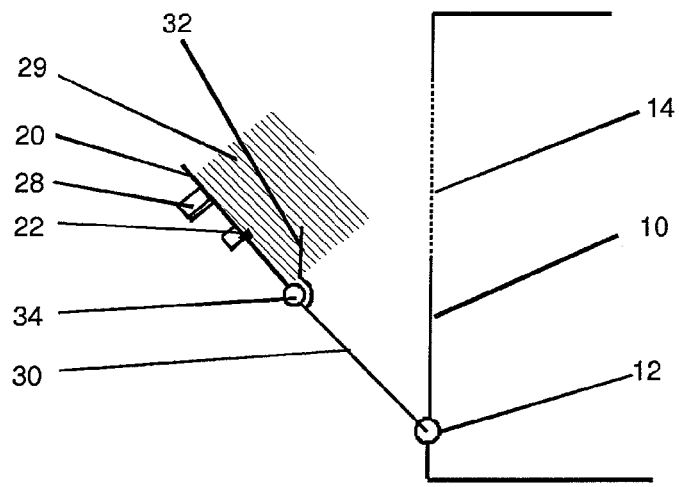
FIG. 1 a schematic diagram of a side elevation of the equipment housing in the third working position, in which the closing flap is open and the closing flap is not vertically aligned, FIG. 2 the schematic diagram in a second working position, in which a locking mechanism holds the closing flap vertical or perpendicular, FIG. 3 the schematic diagram in a first position, in which the closing flap is closed, FIG. 4 an alternative embodiment of the second working position, FIG. 5 an alternative embodiment of the third working position, FIG. 6 a detailed design of the coupling element, FIG. 7 a variant of FIG. 2, with an inclined face of the side wall and FIG. 8 the mounting of the coupling element 30.

The invention is shown in simplified form in the schematic diagram of FIG. 1. This shows a side elevation of a housing wall 10, which is usually designed as the front side of the device, on which are disposed the operating elements 28 accessible to the user. In the housing wall 10 an opening 14 is provided, which is indicated by a dotted line, and via which the service engineer can reach the interior of the device. This opening 14 can be closed by the closing flap 20.

An extracorporeal blood treatment module (EBM) can be disposed on the closing flap 20. Operating and control elements 28 such as pumps, in particular blood and/or heparin pumps, flow meters, displays, valves and shutoff clamps are thereby arranged on the front side of the operating flap of the blood treatment device. On the rear side of the operating flap are arranged the corresponding electrical drive units of the pumps, supply and drain hose system, and electronic control units.

Figure 3:
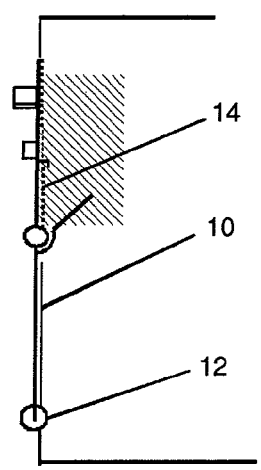
Figure 4:
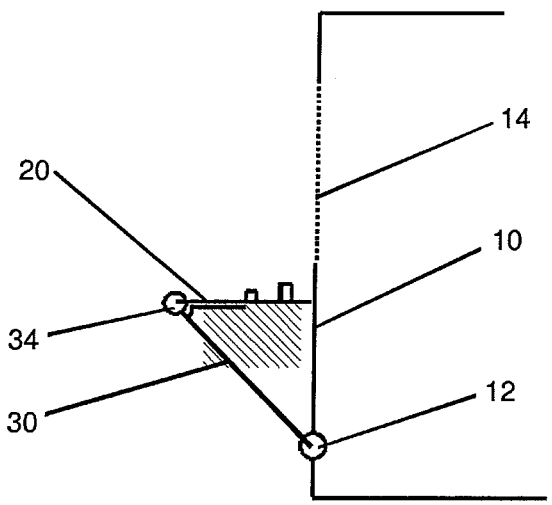

When the closing flap 20 closes the opening 14, the components 29 of the EBM on the rear of the flap are completely accommodated within the device. This corresponds to the normal mode of operation of the device, and is shown in FIG. 3. In a lower part of the closing flap 20 is disposed a center of rotation of a second pivot 34, with which the coupling element 30 engages. This coupling element is realized as a coupling rod or an analogous stamped or laser-cut part (see FIG. 6). This coupling element 30 comprises a lower bearing point, which is mounted with respect to the housing as the first pivot 12. The closing flap is thus pivotable with respect to the housing with the two degrees of freedom of the two pivots 34 and 12. In a practical embodiment the coupling element 30 is preferably realized in the form of two parallel and substantially symmetrical pressed parts, in order thereby to enhance the guiding and torsional stiffness.

From the first closed position shown in FIG. 3, after locking elements such as latches or catches, which are not shown, have been released, the closing flap can be folded out about the first pivot 12 and thereby reaches the third working position corresponding to FIG. 1. In this position the front of the closing flap 20 with the operating and control elements 28 is inclined downwards, and the EBM is outside the housing and easily accessible for servicing purposes from above and the sides. A stop, not shown, between the closing flap 20 and the coupling element 30 ensures that the closing flap 20 does not pivot further downwards due to the action of gravity. Another stop, also not shown, between the coupling element 30 and the housing 10 ensures that the pivoting movement of the coupling element is limited. An arrestor belt or retaining strap 17 can preferably be fixed between the housing 10 and the closing flap 20, and absorb at least part of their weights in the unfolded position (see e.g. FIG. 1).

The pivoting so far described is pivoting about the first pivot 12 only. If the closing flap is now pivoted in the opposite direction about the second pivot axis 34, the closing flap 20 reaches the second opened working position according to FIG. 2, in which the closing flap 20 is vertically aligned, there is still easy access to the EBM, and the operating and control elements 28 are vertically aligned facing forwards. In contrast to the third working position, the operating and control elements 28 are not inclined downwards. In this second working position the service engineer can easily reproduce the user's normal operating processes while simultaneously carrying out the necessary servicing tasks.

The first, second and third positions are each stable states. That is to say that a resistance in the form of a catch must be overcome, or a latch opened, or a movement performed against gravity, in order to bring the closing flap out of this stable position.

It must be emphasized that FIGS. 1-5 are schematic diagrams. Thus for example the second pivot 37 does not have to be disposed under the closing flap 20; instead, the closing flap can also extend below the pivot 34, as is shown by the downwards extension 37 of the closing flap 20 in FIG. 2. Similarly, the pivots can be relocated inwards, so that the corresponding mountings 12 and 34 are completely accommodated in the housing in the closed position according to FIG. 3, and not visible from outside. In FIG. 6, the bearing point of the first pivot 12 shows an example of this.

Figure 5:
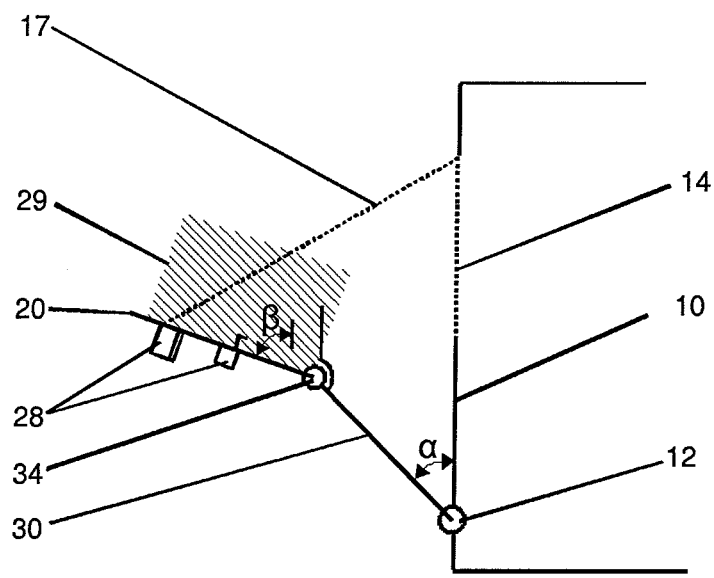
Figure 6:
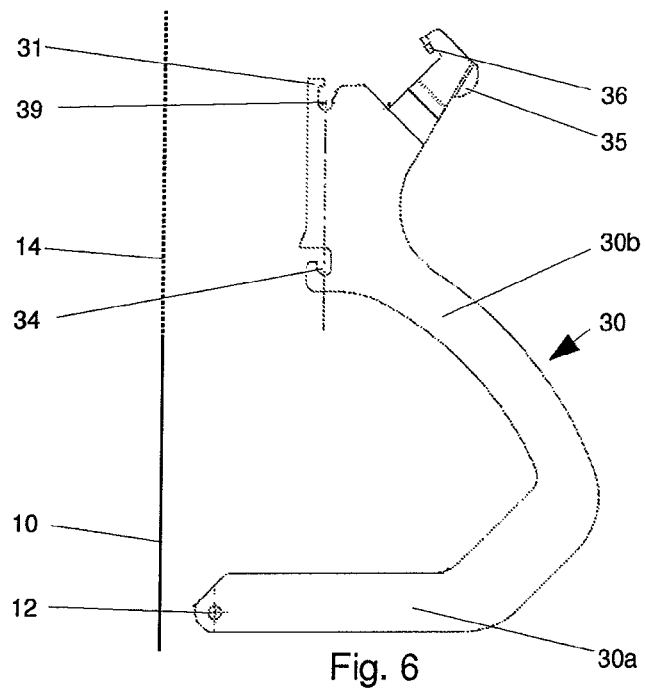

From FIG. 5 an advantage of the invention over the prior art is evident. Designs were known from the prior art with a first pivot 12 and without a second pivot 34. In accordance with FIG. 5 the second pivot 34 allows the opening angle $\beta$ to be greater than the opening angle $\alpha$, so that the service engineer can easily reach the rear side of the EBM from above. This was previously not possible, since due to the limitations on cable and hose length the EBM could not be folded forwards over an increased lower opening angle $\alpha$. Due to the two pivots, a larger opening angle $\beta$ can be achieved, without the EBM being far from the housing.

Figure 2:
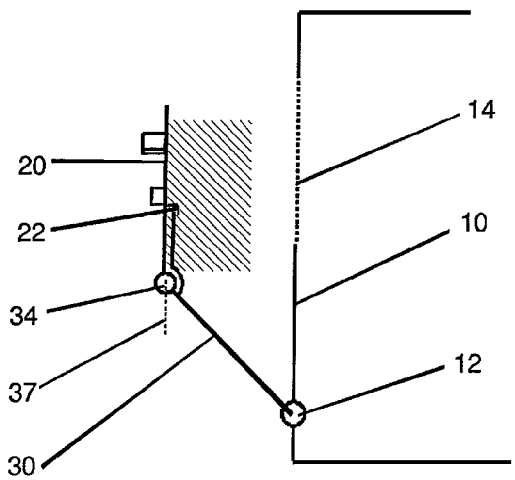

The embodiment according to FIG. 2, in which the closing flap is vertically aligned, is only an example. Other alignments can be also advantageous for servicing, for example +/−10° or +/−30° from the vertical, or the alternative embodiment of FIG. 4, in which the front of the closing flap faces upwards. In the latter case a service engineer can both reach into the interior of the device easily through the opening 14, and simultaneously reach, read and operate the operating and control elements 28 on the closing flap 20.

Figure 7:
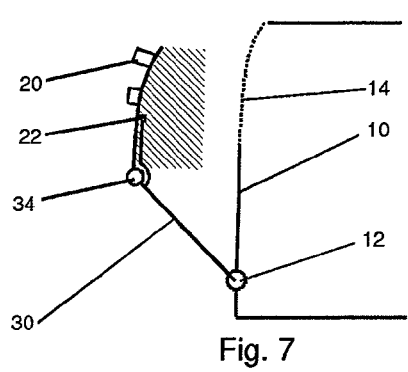

FIG. 7 shows a variant in which the side wall 10 in the region of the opening 14 inclines as it ascends. Additionally it has a curve in the form of a convex contour. This gives the device an attractive optical design, and because the closing flap 20 is at approximately the chest height of a person standing in front of it, it is easier to reach the operating components located on the closing flap. After opening, the angular position of the closing flap, as shown in FIG. 7, is identical to its alignment in the closed state. It has thus been displaced to a parallel position.

FIG. 5 further shows a retaining strap 17, which is on the one end fixed to the housing wall 10 or inside the housing, and on the other end attached to the closing flap 20. This retaining strap is realized as a flexible element, such as a cord, band or belt and is shown in FIG. 5 under tension, thus bearing the weights of the closing flap and the EBM 29 and serving to limit the opening angle $\beta$. The opening angle $\alpha$ can also be limited by means of the retaining strap.

FIG. 6 shows a detailed design of the coupling element 30, of which preferably two identical or symmetrical pieces are used, aligned in parallel and working together to support the closing flap 20. According to the schematic diagrams of FIGS. 1-5 it would appear that the coupling element 30 is also visible in the closed first position. This is, however, not necessarily required, since the coupling element 30 according to FIG. 6 can also be bow-shaped. In this case a lower limb 30a remains always in the equipment housing, while an upper limb 30b can swing through the opening 14 out of the housing for the opened working positions. Thus the visual impression of the exterior of the device below the closing flap is not disturbed by a visible coupling element. FIG. 6 further shows a stop 31, which limits the slot 39 at its top. When the slot 39 is additionally used as a bearing around the pivot 34, the stop 31 ensures that to remove the EBM a double movement, i.e. a lifting and a sideways displacement, must be performed, in order to prevent the EBM accidentally falling out, due for example to a jolt from below.

The coupling element 30 is a stamped and bent component composed of metal of a sufficient thickness, e.g. a minimum of 2 mm+/−1 mm, and has on an upper limb 30b an unlatcher 35, and an angled portion 36 formed by bending, which is engageable with a corresponding stop (not shown) on the closing flap 20 and can thereby hold the closing flap 20 in a vertical working position in accordance with FIG. 2. If the service engineer now presses the unlatcher 25 (in the drawing plane of FIG. 6), the coupling element 30 can elastically deform slightly, so that the angled portion 36 becomes removable from the said stop in the manner of a latch and the closing flap 20 is consequently pivotable about the second pivot 34. In this way both the mounting of the closing flap and also the definition of the working positions can be cost-effectively realized in an integrally formed coupling element 30, for example by a laser-cut component.

Figure 8:
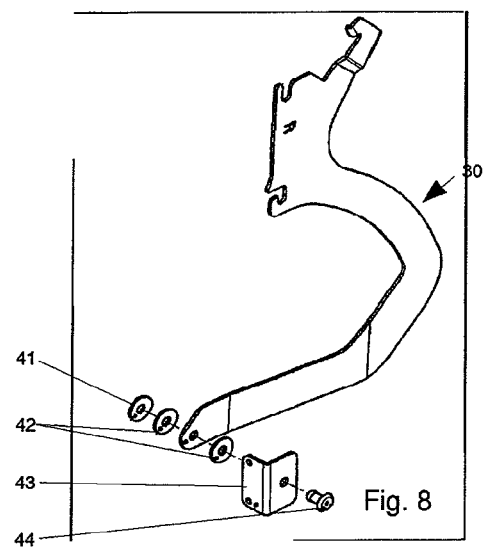

FIG. 8 shows the mounting of the coupling element 30 via a bearing carrier 43, which is attached to, and preferably inside, the equipment housing. On both sides of the coupling element 30 there are plastic washers 42, with an additional washer 41 provided on one side. On the other side a rivet 44 is inserted, which keeps the said elements under axial preload. By this means, along with the mounting a retardation or a certain damping of the coupling element 30 is achieved. Since the EBM has an appreciable weight, of approximately 15 kg, this retardation or damping is expedient, since if the mechanism were undamped large forces would be exerted on its structure when the final position was reached, and the EBM would also be in danger of falling out. The damping can further be assisted by gas pressure springs or dampers (not shown). The plastic washers 42 also facilitate, by the resistance to movement which they exert on the coupling element 30, the guiding of the EBM into the appropriate supports during servicing and assembly work. If a bearing bolt of the EBM is inserted into the corresponding support on the coupling element, this helps the said retardation to hold the coupling element 30 stable.

Features of different embodiments can be freely combined with each other. In particular, the positions and definitions of the various working positions are freely exchangeable, and more than the three stable working positions that were mentioned are encompassed by the idea of the invention.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

The invention claimed is:

1. An equipment housing for a blood treatment device contained therein, said equipment housing comprising:
   a housing wall and a closing flap closing an opening in the housing wall in a first position, said flap having an inner side facing an interior of said housing and an outer side opposite said inner side;
   a coupling element rotatably mounted with respect to the housing wall via a first pivot, rotation of said coupling element outwardly away from the housing wall moving said flap outwardly away from said housing wall to a second working position in which the opening in the housing wall is not closed;
   said closing flap being rotatably mounted with respect to the coupling element via a second pivot; and
   said flap having parts of an extracorporeal blood treatment (EBT) module disposed thereon, said EBT module including at least one of a pump, a flow meter, a valve and a shut-off clamp, at least one of said parts of the EBT module on the inner side of the flap being operationally connected through the flap to another part of the EBT module on the outer side of the flap.

2. The equipment housing according to claim 1, wherein the closing flap can further be disposed in a defined third working position, in which the opening in the housing wall is not closed, by rotating said flap on said second pivot.

3. The equipment housing according to claim 2, wherein the closing flap tends to pivot due to the action of gravity from the second working position into the third working position.

4. The equipment housing according to claim 2, wherein the coupling element of the bow shaped and a lower limb of the bow remains within the equipment housing in all three positions, and an upper limb of the bow in the opened working positions is guided through the housing wall opening out of the housing.

5. The equipment housing according to claim 2, wherein an access area for a service engineer to the opening is greater in the third working position than in the second working position.

6. The equipment housing according to claim 2, wherein in the third working position an opening angle ($\beta$) of the closing flap is greater than an opening angle ($\alpha$) of the coupling element (30) relative to the housing wall.

7. The equipment housing according to claim 2, wherein said flap is configured so that movement thereof both to said second working position and to said third working position creates an access opening to the interior of said housing and also provides access to the parts of the EBT module disposed on the inner side of the flap.

8. The equipment housing according to claim 1, wherein the housing wall is substantially vertically aligned.

9. The equipment housing according to claim 1, wherein the closing flap is not mounted with respect to the equipment housing via any further pivots or coupling elements.

10. The equipment housing according to claim 1, wherein the closing flap is not guided via linear guides with respect to the equipment housing.

11. The equipment housing according to claim 1, wherein a locking mechanism is provided between the coupling element and the closing flap.

12. The equipment housing according to claim 11, wherein the locking mechanism is so arranged that the closing flap in the second working position is aligned substantially parallel to the housing wall when the locking mechanism is in an engaging position.

13. The equipment housing according to claim 11, wherein the locking mechanism is so arranged that the closing flap in the second working position is substantially vertically aligned when the locking mechanism is in an engaging position.

14. The equipment housing according to claim 1, wherein the coupling element or the closing flap has a longitudinal slot in the region of the second pivot, via which the closing flap can be released from the coupling element.

15. The equipment housing according to claim 1, further comprising a second coupling element substantially mirror-symmetrical with and parallel to said coupling element.

16. The equipment housing according to claim 1, wherein operating and control elements for the device are disposed on the outer side of the closing flap.

17. The equipment housing according to claim 1, wherein said parts of said extracorporeal blood treatment module disposed on the flap include at least one of pumps including blood and/or Heparin pumps, flow meters, valves, closing clamps, dripping chambers, tube holders, sensors including pressure-, conductivity-, temperature-, level-, and optical sensors and filters.

18. The equipment housing according to claim 1, wherein the coupling element or the closing flap has a longitudinal slot in the region of the second pivot, via which the closing flap can be removed from the coupling element.

19. The combination comprising:
   an equipment housing for a blood treatment device contained therein, said equipment housing including,
      a housing wall and a closing flap closing an opening in the housing wall in a first position, said flap having an inner side facing an interior of said housing and an outer side opposite said inner side;
      a coupling element rotatably mounted with respect to the housing wall via a first pivot, rotation of said coupling element outwardly away from the housing wall moving said flap outwardly away from said housing wall to a second working position in which the opening in the housing wall is not closed; and said closing flap being rotatably mounted with respect to the coupling element via a second pivot; and parts of an extracorporeal blood treatment (EBT) module disposed on both the inner side and the outer side of said closing flap, at least one of said parts of the EBT module on the inner side of the flap being operationally connected through the flap to another part of the EBT module on the outer side of the flap, said EBT module being operatively associated with said blood treatment device and including at least one of a pump, a flow meter, a valve and a shut-off clamp.

20. The combination according to claim 19, wherein the closing flap is rotatable on said second pivot to be disposed in a defined third working position in which the opening in the housing wall is not closed and the parts of said EBT module on the inner side of the flap are made accessible, said parts made accessible including at least one of pump electrical drive units, a supply and drain hose system and electronic control units.

* * * * *